United States Patent
Mohammad

(10) Patent No.: US 8,586,083 B2
(45) Date of Patent: Nov. 19, 2013

(54) GASTRORETENTIVE DRUG DELIVERY SYSTEM COMPRISING AN EXTRUDED HYDRATABLE POLYMER

(75) Inventor: Hassan Mohammad, Littleport (GB)

(73) Assignee: Euro-Celtique S.A., Luxembourg (LU)

( * ) Notice: Subject to any disclaimer, the term of this patent is extended or adjusted under 35 U.S.C. 154(b) by 275 days.

(21) Appl. No.: 12/554,483

(22) Filed: Sep. 4, 2009

(65) Prior Publication Data

US 2009/0324694 A1    Dec. 31, 2009

Related U.S. Application Data

(63) Continuation of application No. 10/517,858, filed as application No. PCT/GB03/02622 on Jun. 18, 2003, now abandoned.

(30) Foreign Application Priority Data

Jun. 18, 2002 (GB) .................................. 0214013.5

(51) Int. Cl.
*A61K 9/48* (2006.01)

(52) U.S. Cl.
CPC .................................. *A61K 9/4808* (2013.01)
USPC ........................................................ 424/452

(58) Field of Classification Search
None
See application file for complete search history.

(56) References Cited

U.S. PATENT DOCUMENTS

| | | | |
|---|---|---|---|
| 2,531,134 A | 11/1950 | Edward et al. | |
| 4,228,149 A | 10/1980 | Brewer et al. | |
| 4,451,260 A | 5/1984 | Mitra | |
| 4,673,565 A * | 6/1987 | Di Luccio et al. | 424/443 |
| 4,720,384 A * | 1/1988 | Di Luccio et al. | 264/41 |
| 4,758,436 A | 7/1988 | Caldwell et al. | |
| 4,767,627 A | 8/1988 | Caldwell et al. | |
| 4,938,967 A | 7/1990 | Newton et al. | |
| 5,439,966 A | 8/1995 | Graham et al. | |
| 5,582,837 A | 12/1996 | Shell | |
| 5,626,876 A | 5/1997 | Muller et al. | |
| 5,965,161 A | 10/1999 | Oshlack et al. | |
| 6,068,859 A * | 5/2000 | Curatolo et al. | 424/490 |
| 2001/0018070 A1 * | 8/2001 | Shell et al. | 424/469 |

FOREIGN PATENT DOCUMENTS

| | | |
|---|---|---|
| EP | 0717988 | 6/1996 |
| GB | 1601923 | 11/1981 |
| GB | 2249957 | 5/1992 |
| JP | S54-5021 | 1/1979 |
| JP | S58-174312 | 10/1983 |
| WO | WO 99/07342 | 2/1999 |

OTHER PUBLICATIONS

DepoMed's Proprietory Technologies and Products, obtained from http:/www.depomedinc.com/products.html on Jul. 2, 2001.

* cited by examiner

*Primary Examiner* — Bethany Barham
(74) *Attorney, Agent, or Firm* — Davidson, Davidson & Kappel, LLC.

(57) ABSTRACT

According to the present invention there is provided a pharmaceutical product for retention in the stomach. The product is produced by extrusion. The use of extrusion enables the product to take many useful forms. The product may comprise a sheet of hydratable polymer, the hydrated sheet being of a size which will not pass out of the stomach, for example a shaped sheet or a roll. The product may also comprise a scaled hollow tubular extrudate, for example a tube scaled at both ends. The product may comprise a filled capsule.

10 Claims, No Drawings

GASTRORETENTIVE DRUG DELIVERY SYSTEM COMPRISING AN EXTRUDED HYDRATABLE POLYMER

This application is a continuation application of U.S. patent application Ser. No. 10/517,858 filed Dec. 14, 2004, which is a national phase application, filed pursuant to 35 U.S.C. §371, of International Application No. PCT/GB03/02622, filed on Jun. 18, 2003, which claims priority to GB Application No. 0214013.5 filed Jun. 18, 2002, the disclosures of which are incorporated herein by reference in their entireties.

The present invention relates to a pharmaceutical product.

More particularly, the present invention relates pharmaceutical products which are retained in the stomach. In an associated aspect, the invention is concerned with a controlled release drug delivery system for prolonged gastric residence.

BACKGROUND OF THE INVENTION

Although oral sustained release drug delivery systems have attracted considerable attention for the last forty years, technologies for prolongation of gastric residence time of drugs are reasonably recent. Gastric emptying can vary from less than an hour to more than six hours between different subjects and within the same subject. In addition, there is considerable variation in drug absorption from site to site within the gastrointestinal tract. These two aspects can adversely affect the level of bioavailability and the degree of prolongation of an effective plasma level achievable by a conventional sustained release dosage form. Prolongation of residence in the stomach of a dosage form system with sustained drug release properties can have a significant enhancing effect on bioavailability and hence drug effectiveness. Drug being slowly and continuously released at a predetermined rate in the stomach can reach the absorption site in the small intestine in an absorbable state, i.e as a solution or fine dispersion.

During the last 15 years, technologies such as swelling polymers, bioadhesive polymers and inflatable devices in either single or multi-unit systems have been actively investigated. Although drug retention and drug release tested in vitro from most oral prolonged residence delivery systems can be foreseen and maintained between reasonable limits, the lack of in vivo correlation has been evident.

Physiological factors such as pH and motility of the stomach and the fasted and fed state of the subjects have been found to have a profound effect on the gastric residence time of drug delivery systems. Since the stomach is rarely considered a site of drug absorption, most, if not all, sustained release dosage forms have been designed to release the drug through the gastrointestinal tract.

A recent study suggested that the microorganism *Helicobacter pylori* is a major factor in the development of gastric ulcer. It has also been found that about 60% and 40% of the *Helicobacter pylori* are embedded in the fundus and the body regions of the stomach, respectively. For an efficient treatment, a sustained site-specific release of antibiotic to the gastric mucosa is advantageous.

The natural function of the stomach is to temporarily store, mechanically break down and disrupt by acid (hydrochloric acid secreted by parietal cells) and enzyme (pepsinogen secreted by chief cells and converted by the gastric acid into pepsin) the chemical bonds associate with ingested food. The stomach is a hollow elastic organ which varies in shape and size between individuals and in a single individual, depending on size and type of ingested meal.

Anatomically, the stomach may be divided into four main regions:
i) Cardia: the smallest part of the stomach and within 3 cm of the junction with the esophagus. The cardia is rich in mucus glands whose secretion is necessary to protect the esophagus from the acid and enzymes of the stomach.
ii) Fundus: the upper part of the stomach superior to the junction between the stomach body and the esophagus.
iii) Body: the largest part of the stomach, responsible for mixing of ingested food and secretion gastrin.
iv) Pylorus: the lower curved part of the stomach which connects the body with the pyloric canal which empties the stomach content into the duodenum. The pyloric glands are mostly involved in the secretion of mucus.

The stomach activity can be divided into three phases:
v) The cephalic phase in which the secretion of gastric fluids such as acids, enzymes and salts, and the motility of the digestive system is stimulated by seeing, smelling, tasting of or even thinking about food.
vi) The gastric phase, which is a continuity of the previous phase and is promoted with the arrival of food to the stomach. The gastric phase is associated with stomach stress and increase in the secretion of hydrochloric acid and enzymes. In fasting subjects, the stomach pH may be as low as 1.5. Food ingestion (particularly milk) will initially neutralize the stomach content to as high as pH 6.0, (7) during which the saliva amylase continues acting on the carbohydrate. The presence of food in the stomach triggers further secretion of hydrochloric acid, which can continue for up to two hours. Low pH of the stomach content will inhibit the amylase activity to create a new environment for pepsin activity.
vii) The intestinal phase which is usually initiates a few hours after the arrival of food and when the first chyme is delivered to the duodenum. The arrival of the chyme to the intestine triggers new sets of hormones, enzymes and buffers that coordinate the activities.

There are several basic principles by which drug from an oral solid dosage form can be delivered to the stomach for either local or systemic absorption. Each principle has its own advantages and limitations. Amongst these technologies are:
1. Swelling and Expanding Systems.

Dosage forms that swell and change their density in relation to their surrounding, gastric content, can be retained in the stomach content for longer than other conventional dosage forms. In the first instance, the device may sink down in the gastric content and then, by physically changing, may acquire low density and thereby float to the surface. A monolithic device comprising of drug and swelling agent may absorb water and swell to form a soft gelatinous outside surface and float on the surface whilst maintaining its integrity for a pre-determined time. Hydration and swelling alone would not be enough to significantly change the device density. Hence addition of a small amount of fatty material may be necessary to impede wetting and improve floating (4). The level and type of the swelling agent and the fatty substances have a significant effect on the final swelling and floating characteristics of the device. Swelling also significantly increases the dosage form size, which has been found to influence the transit properties. The stomach discharges its contents including the non-disintegrated solid dosage form, through the pylorus into the intestine.

A non-disintegrating solid dosage form of a manageable size for swallowing may freely pass the pylorus. A solid dosage form that can swell fairly quickly in the gastric contents can be retained in the stomach until the size is reduced, for example, by erosion. Such enlarged dosage forms should not block the pylorus and the size reduction should be gradual to prolong its residency. The premature gastric emptying of the dosage form could lead to swelling and obstruction of the duodenum.

There are several contradictory reports on the effect of dosage form size on residency. A definite cut-off size of a dosage form for appropriate gastric retention is very difficult to specify due to fasted, fed and individual variations (5,6).

The most common approach to this type of technology is to encapsulate a core containing drug and swelling agent. Such agents can expand 2-50 fold (7) when gastric fluid permeates through the coat. When all the soluble content is released the device collapses and discharges through the pylorus.

Another approach is a solid dosage form containing drug, swelling agent and one or more erodible polymers such as high viscosity Hydroxy propylmethy cellulose and the acid soluble Eudragit E. In the gastric media the device swollen to a larger size that can not pass through the pylorus until the size is reduced by erosion. The gastric residence time can be prolonged as long as food and water are maintained in the stomach.

The technology has attracted many academic and commercial organisations but so far has failed to be developed into more than one product (8). Intra- and inter-variation between individuals and the difficulty of maintaining the fed state are obstacles which need to be overcome to allow further progression of this technology.

A folded sheet dosage form to increase time residency was a subject of an early patent (24) for veterinary use. Initially the drug is loaded into a water-insoluble diffusable polymer and cast into a thin sheet. The sheet is then manually rolled and fed to the animal either directly or after encapsulation (24). In the stomach the folded sheet reopens to its original size and shape. The opened sheet should be large enough so as not to pass the pyloric sphincter.

Several human studies on the transit of non-disintegrated solid dosage form have shown that the pyloric sphincter can only pass solid object smaller than 8 mm. A similar study has carried out using a non-disintegrating polyethylene geometrical shape (20 mm tetrahedron) spiked with a radioactive marker. The device showed a median retention time of 6.5 hour in fed subjects but a less significant 3 hours median time in fasted subjects (25).

In an animal study, non-disintegrating capsule shaped tablets (22.0×8.5×5.1 mm) were retained in the pig stomach for up to 6.0 hours. In contrast, fine powder and solution was transported out of the stomach in a very fast manner (26).

Therefore, a fully opened rectangular sheet, 10 mm$^2$ or larger in area, should not practically pass the pyloric sphincter unless fragmented or collapsed. The acidic environment and the presence of gastric enzymes could also play a major role in the disruption and elimination of the sheet after a predetermined time of residency. The limitations of this technology are the reproducible cutting, folding, maintaining the shape and filling the folded sheet into capsule shells.

2. Floating and Buoyancing System.

The basic principle of this system is to trap gases within sealed encapsulated cores that can float over the gastric content and so be retained in the stomach for a longer time (9-12). Due to the buoyancy effect, this system can provide a protective layer preventing the reflux of gastric content into the esophageal region and can also be used for controlled release devices.

The development of this system is based on two main techniques. The first system is made of hollow cores containing drug and coated with protective membrane. The trapped air in the cores will help the system to float on the gastric content until all or most of the soluble ingredients are released and the system collapses.

The second system is made of cores that, in addition to the drug, contain chemical substances, which generate gases when activated. Coated cores, for example, containing carbonate and/or bicarbonate generate carbon dioxide in the reaction with the hydrochloric acid in the stomach or incorporated organic acid in the system. The generated and trapped carbon dioxide within the encapsulated core help in floating the device. The inflated device later collapses and clears from the stomach when the generated gas permeates slowly through the protective coat.

The major setbacks of these technologies are the different level of hydration and swelling of the agents under different stomach condition. The gastric pH and presence of water and foods have an unpredictable effect on the swelling agents. The time required for swelling and deflation and/or erosion dictate the successfulness of the system and the gastric residence time. Delay in the swelling or fast deflation or erosion will cause early transit of the device to the duodenum.

It is well observed and documented that presence of food and water in the stomach has a significant effect on the residency of non-floating and floating devices (12-14). A human study of the retention time of floating capsules and tablet devices showed that the devices may be retained for up to 4 hours in fed subjects compared to only 2 hours in fasted subjects (15). Other factors affecting the hydration speed and degree will inevitably change the residence time of the floating dosage form. Film forming polymer should be carefully selected to fulfil specific needs. Film hydration and permeability are two more important factors to be carefully considered. These publications recommend that the film should easily permit water and chloride ion (if it is needed for gas evolution), have good elasticity, and release the drug whilst retaining the evolved gas for a considerable time.

In general the effectiveness of the floating system is determined by the subjects conditions (fast and fed), presence of water and the body state (position) the housekeeper waves (in phase 3 of the interdigestive migrating myoelectric complex, IMMC, which occurs every 1-2 hours (8)), and the device properties, such as size, density, inflation mechanism and other formulation factors.

3. Bioadhesive System.

Intensive studies have been carried out since this approach was first published by Park and Robinson in 1984 (16), on a wide range of natural and synthetic polymers for their bioadhesive properties. Anionic polymers such as sodium carboxy methyl cellulose has a better bioadhesive properties than the neutral and cationic polymers. This finding was disputed later when other cationic polymers were successfully tested (17). Bioadhesive polymers can provide a good vehicle for delivery of drugs to a number of mucosal surfaces in addition to the gastric mucosa. The system can be designed by incorporation of the drug and other excepients within the bioadhesive polymers. On swallowing, the polymer hydrates and adheres to the mucus membrane of the stomach. The mechanism of the adhesion is thought to be through the formation of electrostatic and hydrogen bonding at the polymer-mucus boundary.

A group of researchers (18) have applied the commercially available sucralfate (an aluminum salt of disaccharide used in healing duodenal and gastric ulcer) as a bioadhesive polymer. For a gastric retention system in combination with high viscosity methocel, the compressed tablet was found to adhere to a glass surface and remained intact for at least 24 hours in a 0.1N hydrochloric acid. In this media the sucralfate react with hydrochloric acid to form a very tacky gel. It is believed that sucralfate exerts its healing action not by neutralising the excess acid but by mechanically adhering to the proteinaceous exudate at the ulcer site.

Ideally the muco-adhesive polymer should adhere to the gastric mucus layer until it is removed spontaneously from the surface by various physiological factors. The differences in the physico-chemical nature of these polymers and the variation of inter and intra individual physiological factors such as peristalsis and mucin turnover rate, gastric pH and fast/fed state and type of foods make prediction of removal difficult.

Although there is a substantial amount of literature relating to the gastroadhesive properties of a wide range of polymeric materials, the appropriate successful candidate has yet to be found. Proper selection and evaluation of a successful gastroadhesive polymer involves developing several in vitro and in vivo reproducible methods to quantify the interaction between the polymer and mucosal surface under different extreme conditions. All factors directly and indirectly effecting the adhesion properties should be carefully and intensively studied.

Carbopol and polycabophil were reported to have excellent mucoadhesive properties when tested in animals. Despite these animal successes, test in humans have shown rather disappointing results. Although, there is about a 3 hour delay in gastric emptying in fasted state of animals, there is only 1-1.5 hour delay in fasting humans (19, 20). In spite of the excellent bioadhesive properties of polycarbophole and carbopol through numerous hydrogen bonds provided by the carboxyl group, the disappointing results are believed to be due to the fast turnover of gastric mucin in man.

4. Ion Exchange Resin.

In a published study (21), fast dissolving freeze dried tablets containing an anionic ion-exchange resin (Duolite AP-143) revealed prolonged gastric residence and uniform distribution of the resin within the stomach regardless their particle size distribution. The ion-exchange resin, unlike the water soluble non-absorbable marker diethylenetriamine-penta-acetic acid co-administered with the resin was retained in the stomach for up to 5 hours. It has been suggested that the ion-exchange resin contained in the dosage form may have inherent bioadhesive properties similar to highly charged polymers. As only one in vivo study was carried out, further in vitro and in vivo studies under different physical and physiological condition are required to justify whether the anionic exchange-resin is a suitable candidate as gastroadhesive agent.

In another human study (10,11), radio labeled ion-exchange resin loaded with bicarbonate ions and coated with ethyl cellulose resided in the stomach significantly longer than non loaded ion-exchange resin treated in the same way. In the stomach, chloride ions readily exchange the bicarbonate ions to generate carbon dioxide. The released carbon dioxide inflates the coated membrane, helping the resin to float. The resin keeps floating while there are bicarbonate ions available and ready to exchange with the chlorine ions in the stomach. Prolonging the gastric residence by a floating system increases the chance of drug release in the fundus and cardiac regions of the stomach for local use.

5. Magnetically Controlled Gastric Residence.

A bilayer tablet comprising of a drug layer made of drug, hydroxypropylmethylcellulose, HPMC, and lactose and a magnetic layer made of ultra fine ferrite and HPMC has been developed. Each layer was separately compressed into tablets. The compressed magnetic layer was then coated with water insoluble ethyl-vinyl acetate copolymer. After drying, the coated magnetic layer was stuck to the drug layer with cyanoacrylate-type adhesive.

An in vivo animal study was performed comparing orally administered single layer tablets (drug only layer without the magnetic layer) with bilayer tablets (both the drug and the magnetic layers). To increase the gastric residency time, a magnetic field of 1000-2600 G was applied. The gastric residency and the drug bioavailability of the bilayer tablets were significantly increased by the application of the magnetic field.

In a series of studies, this concept was shown to work but is rather difficult to undertake practically and realise a commercially viable dosage form. Locating the exact position of the magnetic field to the magnetic dosage form in the stomach for each individual may be not easy. In addition, the safety of applying of more than 1000-G magnetic field is unproven.

SUMMARY OF THE INVENTION

According to the present invention there is provided a pharmaceutical product for retention in the stomach. The product is produced by extrusion. The use of extrusion enables the product to take many useful forms.

The technology is a versatile system which can be used to deliver drugs in a sustained release manner for local and systemic absorption. A specially designed pharmaceutical dosage form can be provided, usually a solid of different distinctive shape and size that can remain in the stomach for a predetermined time. During residency in the stomach, drug is released from the system in a sustained manner to provide medication for local and/or systemic use.

A prolonged gastric residence system of this invention can provide the following advantages;
1. Delivery of drugs that act locally such as antacids, enzymes and antibiotics for bacterially caused ulcers.
2. Modified route for drugs that are degraded in the lower part of the intestine which make it unsuitable for a conventional CR formulation. Metoprolol is known to be well absorbed from the large intestine but is also affected by high pre-systemic clearance in the area (1).
3. Improved bioavailability of drugs which (a) are poorly soluble in the high pH environment of the intestine, or (b) have a narrow absorption window.
4. Drugs that are fairly soluble in the acidic media in the stomach could remain in solution even after transit to the alkaline region of the duodenum. Drugs delivered into the higher pH region of the GIT in a sustained low concentration manner will remain in solution or precipitate into a colloidal form regardless of their solubility in the media. Maintaining the low solubility drug in solution or in fine dispersion will have significant influence on its absorption and bioavailability.
5. Drugs that are absorbed from the proximal part of the small intestine, such as nitrofurantoin, riboflavin, levodopa, p-aminobenzoic acid and allopurinol (2,3) are best administered in a gastric retentive device to improve their bioavailability.
6. Controlled release of drugs with site specific absorption limitations. Drugs that are absorbed rapidly from the GIT, such as amoxicillin are best released slowly in the stomach. These drugs can be formulated into a retentive device to expand their therapeutic window.
7. Overall improved bioavailability of drugs by increasing the total gastrointestinal retention time. The ability to retain the dosage form within the stomach would provide a constant stream of supply of the drug over a wider absorption area. This will provide optimum conditions maximizing drug absorption.

8. Effectively using antibiotics with less likelihood disrupting the normal lower intestinal flora.

The treatment of local diseases associated with reflux esophagitis, hiatus hernia and *Helicobacter pylori* infection could benefit from a prolonged release floating system. This system provides mechanical protection to the affected upper region of the stomach in addition to a sustained drug release (i.e. antibiotic) and/or continuous neutralisation of the excess acid. In a recent study (22) it was reported that combined treatment of omeprazol (prostaglandin analogues) 20 mg BD, amoxycillin (antibiotic) 500 mg td, and metronidazole (antimicrobial against anaerobic bacteria) 400 mg td is more effective in eradication of *Helicobacter pylori* and relief of symptoms of non-ulcer dyspepsia than omeprazol alone. The high dose of amoxylilin and metronidazole is required for their systemic rather than local action. The drug transit through the stomach is reported to be about 1 hour. Retention with sustained drug release in the stomach will benefit local action and hence, reduction in the total dose required.

In addition it has been demonstrated (23) that, in 60% of *Helicobacter pylori* sufferers, the organism was found in the fundal region of the stomach, in 45% in the body and in 14% in the gastric antrum (32% having the microorganism in more than one region of the stomach). Therefore, for the majority of sufferers, the *Helicobacter pylori* is in the upper region of the stomach. The floating sustained release device not only provides the drug for local use but also provides the drug where it is needed.

DETAILED DESCRIPTION OF THE INVENTION

In one embodiment, the product of this invention comprises a sheet of hydratable polymer, the hydrated sheet being of a size which will not pass out of the stomach. Typically the hydrated sheet is at least 8 mm by 8 mm, perhaps at least 12 mm by 12 mm. The sheet is made by extrusion of a mix of active ingredient and polymer, along with other optional ingredients. The mix is preferably extruded as a shaped sheet, and for example takes the form of a roll. As it is extruded, the roll is cut to size. The cut roll may then be filled in a capsule. Upon swallowing, the capsule dissolves and the roll rehydrates and unrolls. Other configurations may be employed for the sheet of hydratable polymer, and for example it can be a folded sheet, or otherwise compacted.

The sheets of this invention can be made by melt extrusion. Redesigning only the extrusion mold can produce a prefolded sheet which can either be taken orally directly or after filling into capsules. The opened flat sheet may benefits from both the size enlargement, preventing it from passing through the pyloric sphincter and from the non-disintegrating low density polymer which should aid the floating of the devise. With a range of gel forming polymers, each individual characteristic of buoyancy (high-density differential) and size (larger than 8 mm) can be varied. The opened sheet could combine both the large area and the floating characteristics required for prolonging the residency time in the stomach.

As mentioned earlier, the folded sheet could be filled into capsules using a tablet filling mechanism. The folded sheet dimensions could be varied from 5.0-9.0 mm diameter and 14.2-24.4 mm in length to either match the dimensions for direct delivery or for filling into size 4-0 elongated capsules.

A preferred system comprises of a single folded sheet opened flat upon hydration by the gastric media. The medium to low density polymer and the geometrical size and shape of the sheet grants prolonged residency in the stomach. The presence of water and food in the stomach could be a vital factor in maintaining the buoyancy of both systems necessary for preventing an early transit of the system out of the stomach. The sheet may include acid or enzyme degradable materials, for example polymers, which will eventually be digested and thus change the physica structure, for example by fragmentation of the sheet, and make it susceptible for evacuation with the stomach contents.

In another embodiment, the product of this invention comprises a sealed hollow tubular extrudate. A mix of suitable ingredients including the active ingredient is extruded as a tube, and is cut when still pliable to seal the cut ends, resulting in a hollow particle with active ingredient in the walls. The specific gravity of the particle is such that it floats on gastric juices, and gradually releases the active agent.

This product can be made by melt extrusion. The melt extrusion head can simply be modified to extrude hollow tubes rather than solid strand. These tubes can be made with different inner and outer diameters and can also be cut to any predetermined lengths.

The method of executing cutting while the extrudates (solid strands or hollow tubes) are hot and flexible is called surface cutting. The cutting blades are mounted on the die plate to provide an immediate cut that blinds the cutting edge of the tube while it is still in a semi-melted condition. The produced hollow extrudate tubes provides a low density product with significant buoyancy power. In this dosage form the drug can either be loaded in the tube wall within the protective modified release polymer or can be loosely packed within the tube void using a second single screw extruder mounted on the side of the extrusion head. It is believed that the hollow tube extrudates with two sealed ends will remain buoyant over the stomach contents until the differential density between the dosage form and the content is diminished. This will occur after the drug and other water-soluble components are released from the dosage form. This elimination from the tube wall will create pores allowing water penetration into the tube voids. This will balance the density differential and hence the multiparticulates sink down and are transported with other gastric contents.

Hollow tubes can be heat sealed at both ends. The trapped air within the void provides floating properties to the device. The final density of the proposed solid dosage form will be much lower than the gastric contents. Low glass transition Tg polymers with or without plasticizer (eg: Eudragit RSPO, ethyl cellulose, polyvinyl acetate phthalate and other) can be loaded with the drug and extruded as a hollow tubes. Pelletisation by surface cutting will boost sealing of the two ends of the tubes.

A multi-unit floating device loaded with antibiotic and an acid neutralization capacity can be designed for gastric ulcer treatment caused by *Helicobacter pylori*.

REFERENCES

1. Warrington S J Barclay S P, Jo vV A, Shotton P A, Wardle H M, Good W. 1985 Br. Jour. Clin. Pharmc. 19, 219S.
2. Ichikawa M., Watnabe s., and Miyake Y. 1991 J. Pharm. Sci. Vol. 80, No. 11, 1062-1066
3. Ichikawa M., Kato T., Kawahara M., Watanabe S., and Kayano, M. 1991 J. Pharm. Sci. 80, 1153
4. Oth M., Franz M., Timmermans J., and Moes A., 1992 Pharm. Res. 9, 298.
5. Meyer J H., Dressman J., Fink, A., and Amidon G. 1985 Gastroenterology, 89, 805.

6. Khosla R., Feely L C., and Davis S S., 1989 Int. J. Pharm 53, 107.
7. Deshpande A A., Rhodes C T., Shah N H., and Malick A W., 1996 Drug Dev. Ind. Pharm. 22 (6) 531-539
8. Hwang S J., Park H., and Park K., 1998 Therap. Drug Carrier Syst. 15 (3), 243.
9. Groning R., and Heun G., 1984 Drug Dev. Ind. Pharm. 10, 527.
10. Atyabi F., Sharma H., Mohammad H A H., And Fell J T., 1996 J. Cont. Drug Rel. 42, 25.
11. Atyabi F., Sharma H., Mohammad H A H., And Fell J T., 1996 J. Cont. Drug Rel. 42, 105.
12. Ichikawa M., Watnabe S., and Miyake Y., 1991 J. Pharm. Sci. 80, 1062.
13. Khatar D., Ahuja A., and Khar R. K., 1990 Pharmazie 45, 356
14. Mazer N., Abisch E., Gfeller J C., Laplanche R., Bauerfeind P., Cucala, M., Lukachich M., and Blum A. 1988. J. Phar. Sci. 77, 647.
15. Davis S S., 1986. STP Phar. Pratiques 2, 1015.
16. Park K., and Robinson J R., 1984. Int. J. Pharm. 19, 107.
17. Singla A K Et. Al. 1999 The 18$^{th}$ Pharmaceutical Technology Conference. Page 397
18. Li S P., Pendharkar C M., Mehta G N., Karth M G., and Feld K M., 1993 Drug Dev. Ind. Pharm. 19 (19), 2519.
19. Harris D., Fell J T., Sharma H L., and Taylor D C., 1990 J. Cont. Rel 12, 45
20. Harris D., Fell J T., Sharma H L., and Taylor D C., 1990 J. Cont. Rel 12, 55
21. Burton S Washington N., Steele R J C., Musson R., and Feely L., 1995 J Phar. Pharm. 47, 901-906
22. McColl K Et Al 1998, New Eng. J. med. 339, 1869
23. Altherton J C., Balsitis M., Kirk G E., Hawkey C J., and Spiller R C., 1995 Gut 36, 670.
24. UK Patent 1 601 923 (Beecham Group Ltd) 1977
25. Fix A., Cargill R., and Engle K. 1993 Pharma. Rese. Vol. 10 No. 5 1087
26. Davis s. s., Illum L. and Hinchcliffe 2001 Pharm. Pharmaco. Vol. 53, 33

ADDITIONAL REFERENCES

Agyilirah G A., Green M., duCret R., and Banker G S., 1991
Int. J. Pharm. 75, 241-247
Burns S. J., Corness D., Hay G., Higginbottom S., Whelan I., Attwood D., and Barnwell S G., 1995
Int. J. Pharm. 121, 37-44
Cargill R., Caldwell L J., Engle K., Fix J A., Porter P A., and Gardner C R., 1998
Pharm. Res. .5, .8, 533-536
Chueh H R., Zia H., And Rhodes C T., 1995
Drug Dev. Ind. Phar. 21 (15) 1725-1747
Deshpande A A., Shah N H., Rhodes C T., and Malick W., 1997
Int. J. Pharm. 159, 255-258
Deshpande A A., Shah N H., Rhods C T., Malick W., Al. 1997
Pharm. Res. .14, .6, 815-819
Fujimori J., Macida Y., Tanaka S., and Nagai T., 1995
Inter. J. Pharm. 119, 47-55
Dong L C, 1999
Patent WO9907342-A1
Iannuccelli V., Coppi G., bernabei M T., cameroni R., 1998 (part 1)
Int. J. of Pharm. 174, 47-54
Iannuccelli V., Coppi G., bernabei M T., cameroni R., 1998. (part 2)
Int. J. of Pharm. 174, 55-62
Kawashima Y., Niwa T., Takeuchi H., Hino T., and Itoh Y., 1992
J. Pharm. Scie. .81, .2, 135-140
Longer M A. 1985
J. Pharm. Scie. .74, .4, 406-410
Park K. and Robinson J. R. 1984
Inter. J. of Pharm. 19, 107-127.
Timmermans J., and Moes A J., 1994
J. Pharm. Scie. .83, .1, 18-24
Whitehead L. Fell J T., Collet J H., Sharma H L., Smith A M., 1998
J. Cont. Rel. 55, 3-12

The invention claimed is:

1. A process for producing an oral sustained release drug delivery system which is a pharmaceutical product suitable for retention in the stomach, which process consists of the steps of mixing a hydratable polymer and an active ingredient to give a mix thereof; extrusion of the resulting mix of hydratable polymer and active ingredient using an extrusion mould designed to provide an extrudate with a rolled or prefolded configuration or an extrudate which is a hollow tube, and cutting the extrudate to give a plurality of the desired pharmaceutical product suitable for retention in the stomach selected from rolled sheets, prefolded sheets and sealed tubes.

2. A process according to claim 1, wherein the rolled or folded sheet can be hydrated to give a hydrated sheet of at least 8 mm by 8 mm.

3. A process according to claim 1, wherein the rolled or folded sheet can be hydrated to give a sheet that floats.

4. A process according to claim 1, wherein the sealed tubes float on gastric juices.

5. A process according to claim 1, wherein the rolled sheets, prefolded sheets or sealed tubes are filled into capsules.

6. A product prepared by the process according to claim 1.

7. A process according to claim 2, wherein the rolled or folded sheet can be hydrated to give a sheet that floats.

8. A process for producing an oral sustained release drug delivery system which is a pharmaceutical product suitable for retention in the stomach, which process comprises extrusion of a hydratable polymer using an extrusion mould with an extrusion head designed to provide an extrudate which is a hollow tube, extruding from a second single screw extruder mounted on the side of the extrusion head an active ingredient to loosely pack the tube with the active ingredient, and cutting the extrudate to give a plurality of the desired pharmaceutical product suitable for retention in the stomach in the form of sealed tubes containing active ingredient.

9. A process according to claim 8, wherein the sealed tubes are filled into capsules.

10. A product prepared by the process according to claim 8.

* * * * *